(12) United States Patent  (10) Patent No.: US 9,380,986 B2
Lähelmä  (45) Date of Patent: Jul. 5, 2016

(54) DENTAL SURFACE MODELS (71) Applicant: PLANMECA OY, Helsinki (FI)

(72) Inventor: Jaakko Lähelmä, Helsinki (FI)

(73) Assignee: PLANMECA OY, Helsinki (FI)

( * ) Notice: Subject to any disclaimer, the term of this patent is extended or adjusted under 35 U.S.C. 154(b) by 203 days.

(21) Appl. No.: 13/901,887

(22) Filed: May 24, 2013

(65) Prior Publication Data

US 2013/0330685 A1  Dec. 12, 2013

(30) Foreign Application Priority Data

Jun. 11, 2012  (FI) .................... 20120193
May 10, 2013  (EP) .................... 13167261

(51) Int. Cl.
G06K 9/00 (2006.01)
A61B 6/14 (2006.01)
A61C 9/00 (2006.01)
G06T 7/00 (2006.01)
A61B 6/00 (2006.01)
A61B 6/03 (2006.01)

(52) U.S. Cl.
CPC .............. *A61B 6/145* (2013.01); *A61C 9/0006* (2013.01); *A61C 9/0053* (2013.01); *A61B 6/032* (2013.01); *A61B 6/14* (2013.01); *A61B 6/4085* (2013.01); *A61B 6/582* (2013.01); *G06T 7/0081* (2013.01)

(58) Field of Classification Search
CPC ... A61C 9/0006; A61C 9/0046; G06T 7/0081
See application file for complete search history.

(56) References Cited

U.S. PATENT DOCUMENTS

| 4,710,876 | A | 12/1987 | Cline et al. |
| 5,927,982 | A * | 7/1999 | Kruger ............... A61C 1/084 433/213 |
| 6,243,439 | B1 | 6/2001 | Arai |
| 7,286,954 | B2 * | 10/2007 | Kopelman ........... A61B 5/1077 382/128 |
| 9,198,627 | B2 * | 12/2015 | Suttin ................. A61C 8/0001 |
| 2003/0065259 | A1 | 4/2003 | Gateno |
| 2007/0190481 | A1 | 8/2007 | Schmitt |

(Continued)

FOREIGN PATENT DOCUMENTS

BE  EP 2306400 A1 *  4/2011  ........... G06T 7/0081
EP  1982652  10/2008

(Continued)

OTHER PUBLICATIONS

Hsieh J., Computed Tomography; Principles, Design, Artifacts and Recent Advances, SPIE Publications; $2^{nd}$ revised edition (Nov. 19, 2009), Chapter 4, pp. 119-140.

(Continued)

*Primary Examiner* — Stephen R Koziol
*Assistant Examiner* — Jonathan S Lee
(74) *Attorney, Agent, or Firm* — Fay Sharpe LLP (57) ABSTRACT

To create a digital surface model of an intra-oral anatomy, a recess or a hole in an impression material having a predetermined shape and size is scanned. The scanning results and information on the predetermined shape and size are used for determining a threshold value representing interface between the impression material and another material. The threshold value is then used in generating the digital surface model from CT scanning data of an impression of an intra-oral anatomy on said impression material.

15 Claims, 4 Drawing Sheets

(56) References Cited

U.S. PATENT DOCUMENTS

| | | | |
|---|---|---|---|
| 2009/0042167 A1* | 2/2009 | Van Der Zel | A61C 1/084 433/215 |
| 2010/0075279 A1* | 3/2010 | Ho et al. | 433/215 |
| 2011/0045431 A1* | 2/2011 | Groscurth et al. | 433/74 |
| 2011/0275029 A1* | 11/2011 | Gao | A61C 1/084 433/167 |
| 2012/0028211 A1 | 2/2012 | Palti | |
| 2012/0088208 A1* | 4/2012 | Schulter | A61C 8/0001 433/173 |
| 2013/0273492 A1* | 10/2013 | Suttin, Sr. | A61C 8/0001 433/29 |

FOREIGN PATENT DOCUMENTS

| | | |
|---|---|---|
| EP | 2254068 A1 * | 11/2010 |
| EP | 2368498 A1 | 9/2011 |
| WO | WO 2008051129 A1 | 5/2008 |
| WO | WO 2008083857 A1 | 7/2008 |

OTHER PUBLICATIONS

Search Report from Finnish Patent Application No. 20120193, 2 pages.

* cited by examiner

DENTAL SURFACE MODELS

FIELD

The invention relates to scanning (imaging) dental impressions and particularly to creating a digital surface model of one or more teeth for dental purposes.

BACKGROUND ART

In the field of dentistry, a wide variety of procedures and techniques require fabricating a model of a patient's teeth. Modelling teeth often requires making accurate dental casts of a patient's teeth, tooth surfaces, gingival and other fine details of the patient's dentition. Traditional dental casts are made by inserting a dental impression tray with dental impression material into a patient's mouth and keeping it there until the impression material has sufficiently hardened. Then the tray with the impression material is removed from the mouth, the hardened material now containing an impression of the desired intra-oral surfaces of the patient. The impression may then be used for obtaining a positive 3-D model of the dentition. Nowadays, besides the physical 3-D models like plaster casts of teeth, also digital 3-D models are used. In other words, by means of a computer program, negative dental impressions may be used to generate positive digital models of the dentition.

In order for the digital model to have true therapeutic use, in addition to mere general visualization of the intra-oral surfaces, it should be accurate enough. For example, in orthodontics and with other dentistry operations, such as designing tooth transplantations, occlusion corrections, crowns, a high degree of accuracy and detail of the 3-D model is required so that a crown, for example, will fit into the existing dentition properly. Typically, these 3-D digital models are created by using optic scanners utilizing visible light, such as a laser beam, to provide input to a computer program creating the digital 3-D model from the impression. The reason for using optic scanners is that the accuracy achievable by an optical scanner is in the range of microns, such as 0.01 to 0.05 mm, whereas the accuracy of traditional CT (computed tomography) imaging when creating such surface models is in the range of millimeters. A problem with using optical scanners is that its use does not extend to radiography, meaning in practise that two different imaging devices are needed at a dental clinic in order to be able to properly image both cranial surface and sub-surface features.

SUMMARY

The following presents a simplified summary of the invention in order to provide a basic understanding of some aspects or objects of the invention. This summary is not intended to identify key or critical elements of the invention or to delineate the scope of the invention.

An object of the present invention is to provide novel means for digital 3D modelling of surfaces of dental arch, for example, which does not include irradiating a patient and includes using an imaging technique and apparatus often available at a dental clinic anyhow. The object is achieved by aspects providing to an impression material, in addition to an impression of an intra-oral anatomy, a recess or a hole with a predetermined form and size, and to use information relating to that recess or hole in processing voxel data, or volumetric data, generated in CT scanning of the impression of an intra-oral anatomy for identifying location of a surface, like an air-material interface, of the impression in the voxel representation of the 3D digital model of the impression.

Various aspects of the invention comprise a method, a CT imaging apparatus, a calibration tool and an impression tray, which are characterized by what is stated in the independent claims. Further aspects are disclosed in the dependent claims.

Advantages provided by one or more aspects of the invention includes making it possible to generate accurate digital 3D models by CT or CBCT scanning of an impression. Another advantage is that an CT or CBCT imaging apparatus which is basically designed for other imaging purposes than creating 3-D surface models of dental impressions can be used so that one does not need to acquire a separate optical scanning device in order to be able to create accurate enough digital 3D surface models from the area of the dental arch.

BRIEF DESCRIPTION OF THE DRAWINGS

In the following, different embodiments and advantages of the invention will be described in greater detail with reference to the attached drawings, in which.

DETAILED DESCRIPTION OF SOME EMBODIMENTS

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

The present invention is applicable to any imaging based on computed tomography (CT). In the following, different embodiments will be described using, as an example of an imaging technique, a cone beam computer tomography CBCT without restricting the embodiments to such a technique, however.

CBCT is one form of computed tomography. In the CT imaging, the volume to be imaged is irradiated by means of a beam from different directions and from the image data thus acquired, a desired two- or three-dimensional image is reconstructed. In CBCT, a cone-like beam is used the size of which substantially corresponds to the volume to be imaged, and a detector the size of which corresponds to the size of the beam being used. However, the implementation details of CBCT, or any other form of CT, are not relevant for understanding and implementing the invention and are therefore not discussed in detail here.

Figure 1:
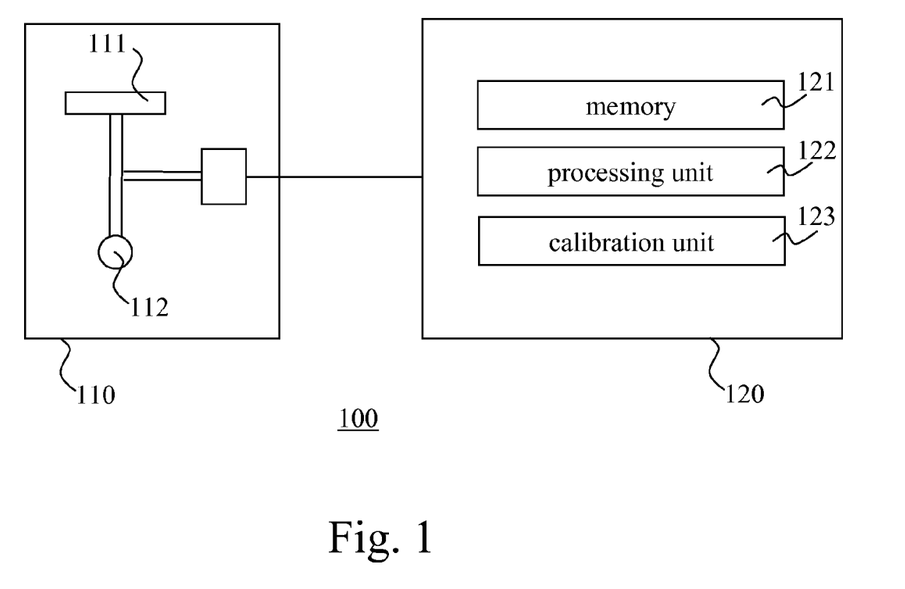
FIG. 1 is a simplified block diagram illustrating a system used as an example and a schematic diagram of an imaging apparatus.

An example of a general architecture of a system 100 for creating a digital 3-D surface model is illustrated in FIG. 1. The system includes a CBCT scanner 110 as an imaging apparatus, the CBCT scanner comprising a detector 111 and a radiation source 112. The CBCT scanner may be for example an imaging apparatus called Planmeca ProMax®, manufactured by the applicant of this application.

During a CBCT scan of a dental impression, for example, the detector 111 and the radiation source 112 rotate around the object to be scanned (not illustrated in FIG. 1) and about 600 distinct images, for example, are obtained. In the illustrated example of FIG. 1, the image data thus acquired is stored to a memory 121 of a computing apparatus 120. A scanning results processing unit 122 (processing unit) collects the data and numerically reconstructs it, producing digital volumetric data composed of three dimensional pixels (voxels) of the object, which can then be manipulated and visualized with specialized units (not illustrated in FIG. 1).

The computing apparatus 120 of FIG. 1 further comprises a calibration unit 123 configured to process data generated by the scanning results processing unit 122. The calibration unit 123 is configured to provide a threshold value (a separation criterion), as will be explained in more detail below. The memory 121 may further be configured to store information on one or more calibration tools 200, which will be discussed in more detail below.

In the illustrated example of FIG. 1, the computing apparatus 120 and the scanner 110 are connected to each other over a fixed connection. It should be appreciated that they may be connected to each other over the air wirelessly, by means of Bluetooth or wireless LAN, for example, or they may be integrated into one apparatus. Further, image data obtained by the scanner 110 may be stored to a detachable memory, such as one arranged in the scanner 110, and transferred by means of the detachable memory to the computing apparatus 120, in which case there is no direct connection between the scanner 110 and the computing apparatus 120.

The computing apparatus 120 may be any computing apparatus by which image data obtained by CT or CBCT scanning can be accessed and processed to determine a threshold value, as will be discussed below in more detail. The processing includes creating a 3-D digital surface model by means of the threshold value and image data of the object. Examples of such a computing apparatus include a work station, such as a laptop or a personal computer. In other words, the computing apparatus 120 is a computing device comprising not only prior art means, but also means for implementing a functionality described with an example, and it may comprise separate means for each separate function, or means may be configured to perform two or more functions, and even to combine functions of different examples. These means may be implemented by various techniques, such as by hardware (one or more apparatuses), firmware (one or more apparatuses), software (one or more modules), or combinations thereof. For firmware or software, implementation can be through units/modules (e.g., procedures, functions, and so on) that perform the functions described herein. Each of the units, like the scanning results processing unit 122 and/or the calibration unit 123 may be a separate unit or integrated to another unit, or the units may be integrated together. For example, the scanning results processing unit 122 and/or the calibration unit 123 may be integrated to be part of the control system described in the above mentioned European patent application EP12160609 and Finnish patent application no. 20110106.

A computing apparatus implementing a functionality or some functionalities according to an example may generally include a processor (not shown in FIG. 1), a controller, a control unit and a micro-controller or the like connected to a memory and to various interfaces of the apparatus. Generally, the processor is a central processing unit, but the processor may also be an additional operation processor. The scanning results processing unit 122 and/or the calibration unit 123 may be configured as a computer or a processor, or a microprocessor, such as a single-chip computer element, or as a chipset, including at least a memory for providing storage area used for arithmetic operation and an operation processor for executing the arithmetic operation. The scanning results processing unit 122 and/or the calibration unit 123 may comprise one or more computer processors, application-specific integrated circuits (ASIC), digital signal processors (DSP), digital signal processing devices (DSPD), programmable logic devices (PLD), field-programmable gate arrays (FPGA), and/or other hardware components that have been programmed to carry out one or more functions of one or more examples. An embodiment provides a computer program embodied on any client-readable distribution/data storage medium or memory unit(s) or article(s) of manufacture, comprising program instructions executable by one or more processors/computers, which instructions, when loaded into an apparatus, constitute the scanning results processing unit 122 and/or the calibration unit 123. Programs, also called program products, including software routines, program snippets constituting "program libraries", applets and macros, can be stored in any medium and may be downloaded into an apparatus. The memory 121 may be implemented within the processor/computer or it may be external to the processor/computer, in which case it can be communicatively coupled to the processor/computer via various means, as is known in the art. The memory 121 may be volatile and/or non-volatile memory, for example EEPROM, ROM, PROM, RAM, DRAM, SRAM, firmware, programmable logic, double floating-gate field effect transistor, etc. and it may also store other data.

Although the computing apparatus 120 has been depicted as one unity, different processors, controllers, interfaces and/or memory/memories may be implemented in one or more physical or logical units.

Figure 2:
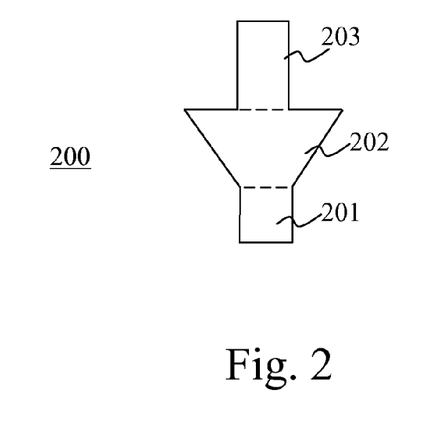
FIG. 2 is a side view of an exemplary calibration tool.

FIG. 2 is a side view of an exemplary calibration tool 200 which can be used in the context of the invention. This exemplary calibration tool comprises a first part 201, a second part 202 and a third part 203, the parts being separated in the FIG. 2 by a dashed line, although in real life the parts preferably are not physically separate. The first part 201 is a part intended to be inserted into the impression material, the first part 201 forming a recess or a hole in the impression material having a predetermined size and shape (dimensions). The first part 201 has preferably, but not necessarily, a form of a cylinder. The second part 202 is a transitional part which may be partly inserted into the impression material, the main function of the second part 202 being ensuring that the recess or hole formed to the impression material by means of the calibration tool 200 is deep enough. Further, the second part 202 may be used to detect the end of the first part 201 in the recess. Therefore, in the illustrated example, the second part 202 has a conical form. However, there are no limitations to the form of the second part 202, if the calibration tool 200 has such a transitional part to begin with. Further, it is not necessary that the second part 202 extends outwards from the first part 201. The second part 202 may be a groove, for example. The third part 203 is arranged in the calibration tool 200 for removing the calibration tool 200 from the hardened impression material and naturally also for inserting the calibration tool 200 in the impression material. Dimensions defining the shape and size of the first part 201 are stored to the memory 121 as information of the calibration tool 200. If the calibration tool 200 is designed using a computer aided design program or a drawing program, the dimensions of the calibration tool 200 may be obtained from the design of the calibration tool 200.

The first part 201 of the calibration tool 200 may be dimensioned so that it is about the same size as the objects whose surface is to be generated based on the calibration. In other words, even though the size of the recess or the hole to be created in the impression material is not that critical considering determining the threshold value according to the invention, in view of implementing the invention in the context of dentistry, in practise, it would be convenient to have the first part 201 dimensioned close to the size of an individual tooth.

Although the calibration tool 200 illustrated in FIG. 2 has three parts, it should be appreciated that a calibration tool with another shape can be used, the simplest shape being a peg with one cross sectional shape, like a cylinder. It suffices that there is a structure with predetermined dimensions so that a predetermined surface (recess) can be created in the impression material, for the purpose described in more detail in connection with FIGS. 4 to 6.

It should be appreciated that although no more than one calibration tool design is needed to implement different embodiments and examples of the invention there may be different calibration tool designs for different purposes.

The calibration tool 200 may be made of any suitable material that will not adhere in an undesired way to the impression material so that removing the tool from the hardened impression material will succeed without breaking the recess or hole it has created to the impression material. An example of such a material is aluminium. Further, different parts of the calibration tool may be made of different materials.

The process of creating an impression of teeth starts with selecting an impression material (mass) and an impression tray 300 which are proper for the purpose in question at a given instance. After that, the impression tray 300 is filled with a suitable amount of impression material, and the impression tray 300 with the impression material is positioned in a desired location inside a patient's mouth. When the patient then bites on the impression material in the tray, recesses which will create an impression of the patient's dentition will be formed in the impression material.

When the impression material has hardened enough, the impression tray 300 is removed from the patient's mouth. After that, the impression (a negative, physical 3-D model) is ready for later use.

Then again, to provide impression material with a calibrations recess or hole to be used for determining a threshold value according to the invention, a calibration tool 200 is inserted into the impression material so that at least said first part 201 of the calibration tool 200 having a predetermined form and size is submerged in the impression material. When the impression material has hardened, the calibration tool 200 is removed from the impression material resulting in formation of a calibration recess or hole in the material. After that, the calibration recess or hole is ready for later use.

The calibration recess or hole may be created separately from the creation of the impression of an intra-oral anatomy, or they can be created simultaneously or even integrated. In other words, one can create a calibration recess or hole for a certain impression material separately, but the calibration recess or hole may also be created at the same time when the actual impression of a dentition is made. The calibration recess or hole may even be made using the same impression tray 300 which is used to acquire the impression of an intra-oral anatomy. For example, a separate calibration tool 200 may be inserted to the impression material on the tray 300 after it has been filled with the material, before positioning the tray 300 into the mouth.

Further, it is possible to drill or otherwise machine a calibration recess or hole with predetermined shape and dimensions into a hardened impression material. Yet another alternative is to integrate a calibration tool 200 with an impression tray 300.

Figure 3A:
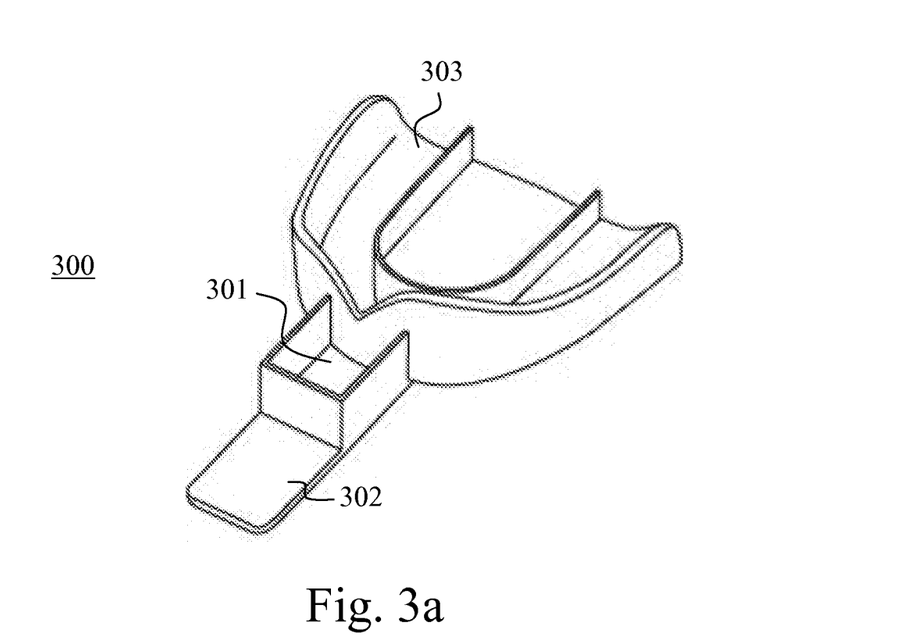
FIGS. 3a and 3b illustrate exemplary impression trays.
Figure 3B:
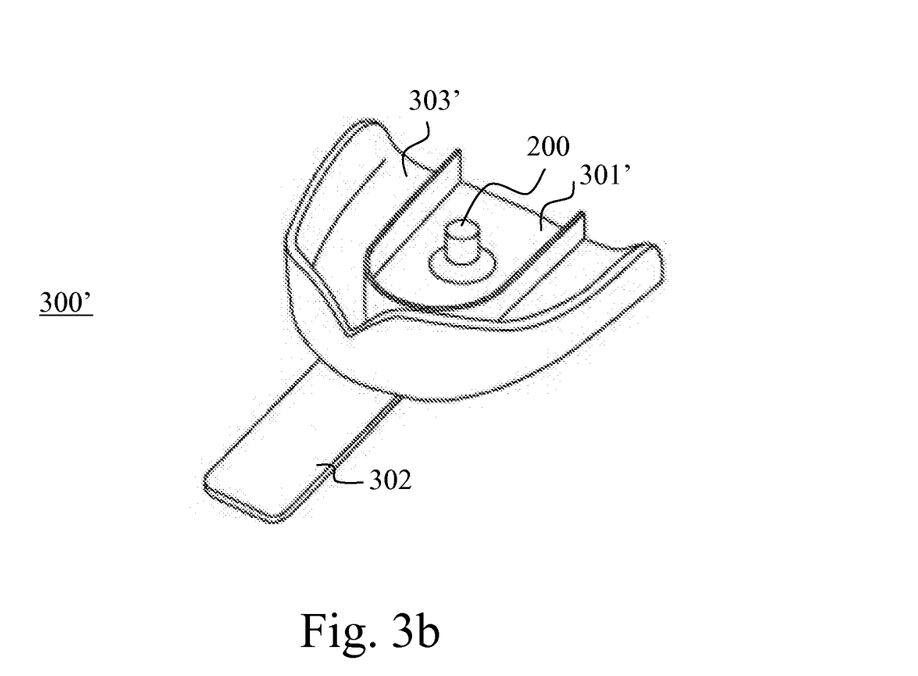

FIGS. 3a and 3b illustrate examples of impression trays 300, 300' facilitating obtaining the recess or hole for defining the threshold value. However, it should be appreciated that prior art impression trays, or platforms specifically designed for that purpose only, may also be used when creating a recess or a hole in the impression material for determining the threshold value.

In addition to a volume 303 for the impression material for teeth, the impression tray 300 illustrated in FIG. 3a is provided on a frontal handle 302 of the impression tray 300 with a volume 301 for the impression material and the calibration tool 200. When an impression of an intra-oral anatomy is taken, it will be easy to simultaneously fill the volume 301 with the impression material and insert the calibration tool 200 into the impression material in the volume 301. In one implementation (not shown here), a calibration tool 200 is connected to the tray 300, for example, by means of a line connected to the frontal handle 302 of the impression tray 300. This ensures that the calibration tool 200 is easily available when an impression is to be made.

In the tray 300' illustrated in FIG. 3b, the volume 301' for the impression material to create the calibration recess is surrounded by the volume 303' for the impression material for teeth, that is, said volume 303' for teeth is of a shape of an arch and said volume 301' for the impression material and the calibration tool 200 is arranged in an area inside that arch. The impression tray 300' comprises inside the volume 301' for the impression material a calibration tool 200 for creation of a calibration recess or a hole.

One calibration tool design may be used for any tray 300, 300' comprising the calibration tool 200 so that the size and shape of the calibration recess or hole will always be the same. On the other hand, tray type specific calibration tool designs may be used as well and information relating to the calibration tools 200 then stored for each tray type. A user may input to the computing apparatus 120 information on the tray type used so that proper calibration dimensions may be acquired. An advantage provided by an impression tray 300' comprising a volume 301' including the calibration tool 200 is that such design facilitates obtaining the calibration recess or hole and makes it easy to ensure that the recess or hole and an impression of the intra-oral anatomy have been made in the same impression material.

It should be appreciated that different types of impression trays 300, 301' may be arranged to contain a volume 301, 301' for the calibration tool 200, and/or both such a volume 301, 301' and the calibration tool 200 itself.

Radiographic scanning of a dentition typically takes place by rotating the imaging means about an axis orienting at right angles to the plane of the dental arch, and the dental impressions and also the calibration recesses or holes created in the impression material may be scanned accordingly. Still, one further possibility is to position the impression and/or the calibration recess or hole in relation to the imaging means such that the recess(es) or the hole will be orientated at right angles to the rotation axis of the imaging means—meaning, in practise, such that at least at some stage of the imaging scan, the radiation beam will be parallel with the orientation of the recess(es) or the hole.

Figure 4:
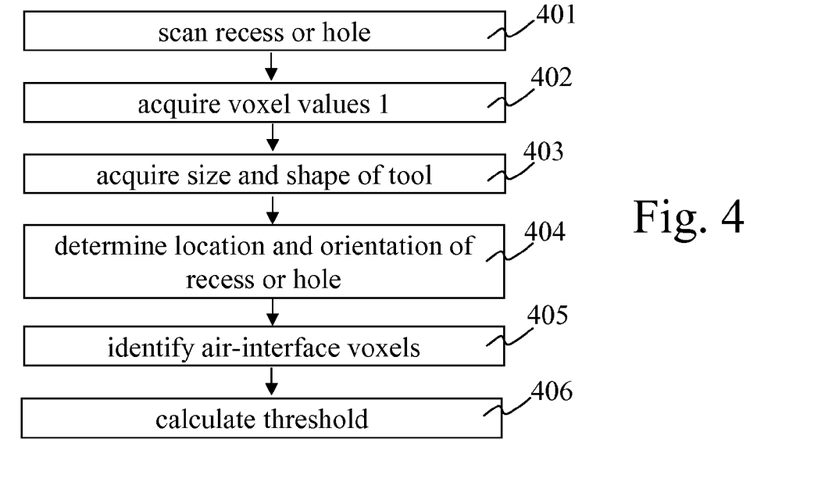
FIGS. 4, 5 and 6 are flow charts illustrating functionality of examples.
Figure 5:
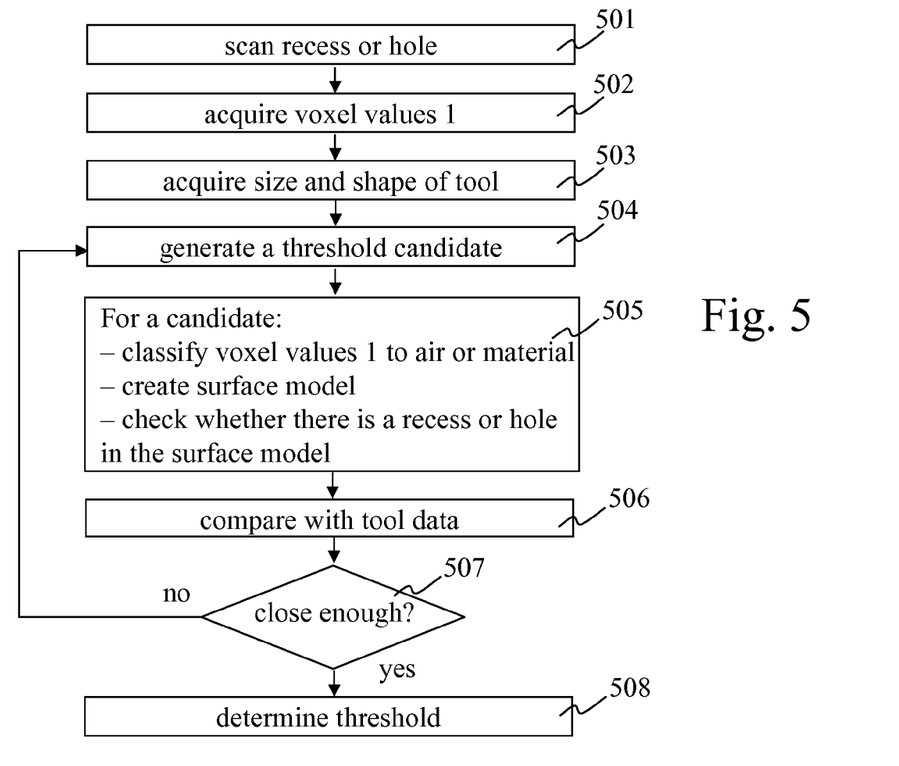

FIGS. 4 and 5 illustrate examples of how a threshold value for use in generating a digital dental surface model may be obtained from information relating to the recess or the hole (of air) produced by the calibration tool to a piece of impression material. In the illustrated examples, shape and size are used as examples of dimensions of the calibration tool 200 which have been stored in the memory 121.

In the illustrated example of FIG. 4, the recess or the hole a calibration tool 200 has left in the impression material is scanned in step 401 by a CBCT scanner, and scanning results (voxel values 1) are acquired in step 402. Then, information of the size and shape of the calibration tool 200 that has been stored in the memory 121 is acquired in step 403. The size may be given as a cross section dimension, like a diameter or a radius of a cylinder (of said first part 201 of the calibration tool 200). Then the actual location and orientation of the recess or hole in the voxel presentation is determined in step 404 by means of pattern recognition. The location and orientation can be determined by other means as well, like maximizing an object function. The object function may be a difference between a mean value of the voxels inside the border of the recess or the hole and a mean value of the voxels outside the borders of the recess or the hole. Using the acquired voxel values 1, the shape and size information of the recess or the hole and the location and orientation determined in step 404, the location of the air-material interface of the recess or hole in the image data can be determined and, thus, the voxels locating on the air-material interface identified in step 405. A threshold value is then calculated in step 406 from the values of the voxels which have been identified to be located on the air-material interface. The threshold value may be an average or a median, or a weighted average, calculated from these values. It is also possible to use just a part of these voxel values in calculation of the threshold value. The threshold value will then be used in creating a surface model of dentition, as will be explained in more detail below.

In the other illustrated example of FIG. 5 to determine a threshold value, the recess or a hole a calibration tool 200 has left in the impression material is scanned in step 501 by a CBCT scanner and scanning results (voxel values 1) are acquired in step 502. Further, the information regarding the size and shape of the calibration tool 200 having been stored in the memory 121 is acquired in step 503. The size may be given as a cross section dimension, like a diameter or a radius of a cylinder (of said first part 201 of the calibration tool 200). Then, candidates for threshold values are chosen in step 504. The candidates may be chosen within the range of the voxel values 1 acquired in the scanning step 501. The threshold candidates may be received as a user input, and/or they may be generated by the calibration unit 123. Preferably the candidates are selected in sequence. A candidate may be one of the actual voxel values 1, but in practise the most appropriate threshold value will most probably be found amongst values in between individual voxel values 1, meaning that candidates having values between the voxel values 1 need to be generated as well. It should be appreciated that the way the threshold candidates are chosen bears no significance and any suitable way may be used.

After one or more candidates have been chosen, the following sub steps are performed in step 505 for a chosen threshold candidate:

The voxel values 1 are classified (labelled) by taking a voxel value and comparing it with the threshold candidate: If the voxel value is above the value of the threshold candidate, it is determined that the voxel locates in (i.e. represents) the impression material, otherwise it is determined that the voxel locates in the air.

A surface model is generated from the classified voxel values 1. The surface may be generated by using a marching cubes algorithm, or any other corresponding algorithm.

It is checked from the surface model thus generated whether or not there is a recess or a hole (i.e. whether a recess is found from the surface model).

When these steps have been performed for the selected threshold candidate, or a set candidates the recesses or holes found, if any, are compared in step 506 with the size and shape of the calibration tool 200 that was acquired in step 503. If amongst the recesses or holes thus found there is a one having a size and shape that is close enough to the size and shape of the calibration tool 200, i.e. the predetermined size and shape of the recess or the hole (step 507), the corresponding threshold candidate is determined in step 508 to be a threshold value. Still, the process may return to step 504 and continue with a new (or a new set of) threshold candidate(s). Then again, in case no recess or hole is found from the surfaces generated in step 505, or none close enough to the dimensions of the calibration tool, i.e. in case nothing is found that can be considered to be close enough to the true size and shape of the recess or hole in the impression material, the process continues again from step 504 to select yet another threshold candidate, or a set of them. Thus, the process illustrated in FIG. 5 is a kind of trial-and-error process.

When using the process of FIG. 5, the user may determine a required accuracy for the 3-D surface model to be generated or a desired accuracy may be set in the calibration unit in advance so that when the calculated size and shape of the recess or hole is close enough to the dimensions of the calibration tool 200, the search for the threshold value may be ended. Further, while it is possible to go on generating sets of candidates for steps 505-507 of the procedure, it is also possible to always select just one and repeat the steps 505-507 until an acceptable candidate has been found. It is further possible to search for more than one candidate fulfilling a predetermined selection criterion and then calculate out of those the threshold value to be used in creating a surface model of dentition, as will be described below.

The examples illustrated in connection with FIGS. 4 and 5 describe alternatives for how to determine a threshold value for the air-material interface for a specific impression material, but other ways to determine the threshold value may be used as well. For example, in the method according to FIG. 4, the location and orientation of the recess or hole may be determined using appropriate error functions and various optimization algorithms and. By means of the threshold value, one is then able to determine the air-material interface of an impression of an intra-oral anatomy in the same material, this procedure providing a means to increase the accuracy of modelling surfaces based on CT and CBCT scanning of dental impressions. Depending on an implementation, a threshold value for a certain impression material may be stored to a memory to be used later when imaging dental impressions on the same impression material, or the process may continue directly according to FIG. 6 as will now be described here.

Figure 6:
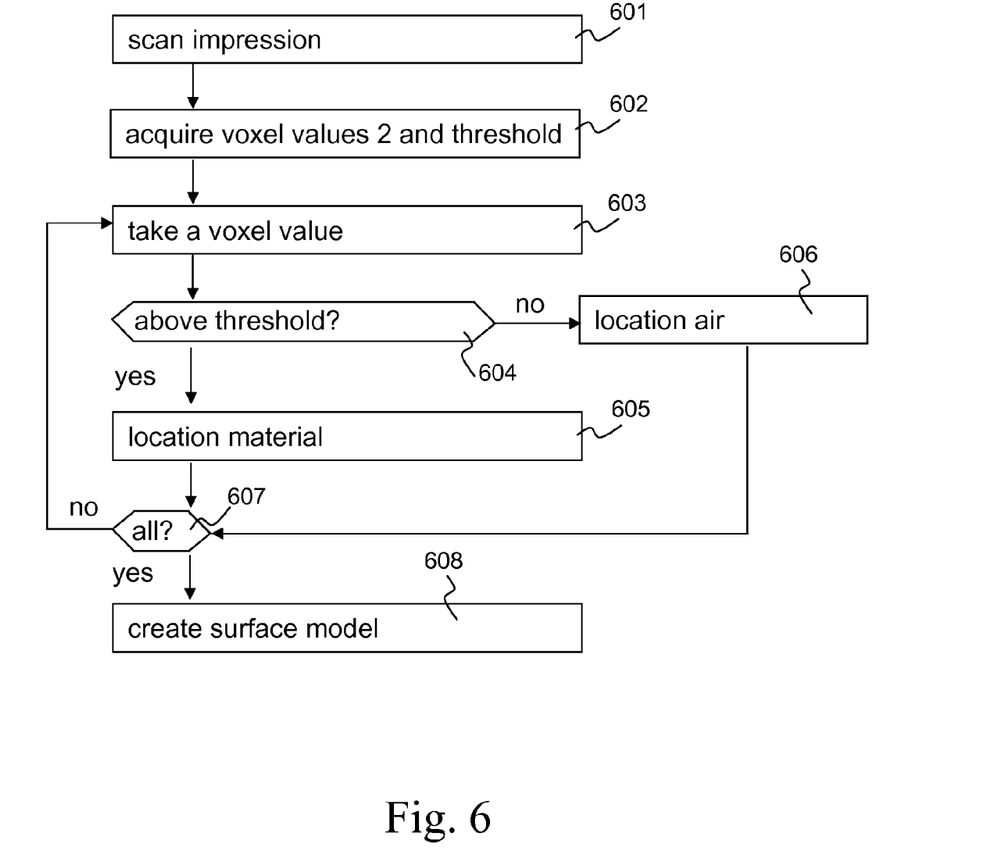

FIG. 6 illustrates an example of how a 3-D surface model of an intra-oral anatomy may be created from the impression of the intra-oral anatomy. In the illustrated example, it is assumed that the material other than the impression material is air and voxel values representing air are smaller than voxel values representing the impression material.

An impression of an intra-oral anatomy is scanned in step 601, and the scanning results of the impression are acquired in step 602. In the illustrated example, the scanning results are acquired as voxel values 2 forming a voxel presentation of the scanned impression. Since in the illustrated example it is assumed that the threshold value has already been determined separately, the threshold value for the impression material is just acquired, e.g. from the memory 121, in step 602.

The voxel values 2 are then classified by taking a voxel value in step 603 and comparing it in step 604 with the threshold value. If the voxel value is above the threshold value, it is determined that the voxel locates in (i.e. represents) the impression material (step 605), otherwise it is determined that the voxel locates in the air (step 606). After that it is checked in step 607, whether or not all voxel values 2 have been processed and in case not, the process continues to step 603 to take an unprocessed voxel value.

After all the voxels have been classified, a surface model of the impression is created in step 608. The surface may be created by using a marching cubes algorithm or any other corresponding algorithm. When this process is made based on the calibration process for a given impression material as discussed above, it is possible to create a digital 3-D surface model of dentition with an accuracy of the order of microns.

Since there is no sharp fall in the voxel values at and around the edges of a digital model of a dental impression, i.e. in the data from scanning a dental impression, it has been difficult to determine from the (CB)CT voxel data alone the exact location of the surface of an impression. Thus, determining location of the surface of an impression has only been possible based on estimating or educated guessing, but by means of the threshold value generated according to the invention one is now able to determine quite accurately where the surface of a dental impression in the digital model should locate.

Although in the above examples the threshold value represents the impression material—air interface, it should be appreciated that a threshold value may be determined relating to other material pairs as well, like the impression material and a material other than air.

The steps shown in FIGS. 4 to 6 are not necessarily in an absolute chronological order, and some of the steps may be performed simultaneously or in an order different from the given one. It may also be possible to combine or divide the steps of FIGS. 4 to 6 into several parts. Other functions can also be executed between the steps or within the steps. For example, if there are different designs for the calibration tools, the process described may comprise choosing a proper calibration tool for the purpose the impression is made, and the processes described in connection with FIGS. 4 and 5 may comprise receiving or acquiring information on the design of the calibration tool used. Some of the steps can also be left out. Further, steps in different Figures may be performed simultaneously or overlapping each other. For example, the recess and an impression of an intra-oral surface may be scanned simultaneously or one after another, and the data stored for later retrieval, i.e. steps 401,501 or 601 may be performed separately from the other steps of the corresponding process. Further, the process of FIG. 4 or FIG. 5 may be integrated to the process of FIG. 6 in which case there is no need to acquire in step 602 the threshold value determined just before. However, it should be appreciated that calibration, i.e. determining the material-specific threshold value, needs to be performed for a given impression material in order to be able to get as accurate results as possible.

It will be obvious to a person skilled in the art that, as the technology advances, the inventive concept can be implemented in various ways. The invention and its embodiments are not limited to the examples described above but may vary within the scope of the claims.

The invention claimed is:

1. A method for generating a digital surface model depicting an interface between an impression material and another material from volumetric data including image data of a physical impression of an intra-oral anatomy, the method comprising without reliance on optical scanning:
   acquiring information defining predetermined dimensions of a recess or a hole in the impression material, said recess or hole being created in the impression material prior to its hardening by inserting a calibration tool having the predetermined dimensions;
   acquiring CT scanning results of said recess or hole in the hardened impression material;
   using said information defining the predetermined dimensions and said CT scanning results of said recess or hole to determine a threshold value for an interface between the impression material and the other material;
   acquiring CT scanning results of the physical impression of an intra-oral anatomy, the impression being made in the same impression material as the recess or hole; and
   using said threshold value in generating a surface of said impression of an intra-oral anatomy from said scanning results of said impression of an intra-oral anatomy.

2. A method as claimed in claim 1, wherein said recess or hole and said impression of the intra-oral anatomy are obtained at least substantially simultaneously.

3. A method as claimed in claim 1, wherein determining said threshold value includes:
   determining location and orientation of said recess or hole in said scanning results of said recess or hole;
   using the predetermined dimensions of said recess or hole and the determined location and orientation thereof to identify from the CT scanning results of said recess or hole the voxels located on an interface of the recess or the hole; and
   calculating the threshold value from the identified voxels.

4. A method as claimed in claim 3, wherein location and orientation of said recess or hole is determined by means of pattern recognition, or an optimization algorithm and an error function.

5. A method as claimed in claim 3, wherein the calculated threshold value is one of the following: an average of the voxels identified to locate on the interface, a weighted average of the voxels identified to locate on the interface, and a median value of the voxels identified to locate on the interface, an average of a part of the identified voxels identified to locate on the interface, a weighted average of a part of the voxels identified to locate on the interface, and a median value of a part of the voxels identified to locate on the interface.

6. A method as claimed in claim 1, wherein determining said threshold value includes steps:
   selecting a candidate or candidates for the threshold value;
   generating from said CT scanning results of said recess or hole a surface using the candidate for the threshold value;
   checking the generated surface to find a recess or a hole;
   comparing dimensions of the recess or hole found in the generated surface with those of the recess or hole of the predetermined dimensions;
   determining the candidate by which a surface having a recess or a hole with dimensions closest to the predetermined dimensions is generated, or the candidate or candidates fulfilling a predetermined selection criterion by which a surface having a recess or a hole close enough to the predetermined dimensions is generated;
   selecting the value of said candidate, or a value calculated from the values of a number of said candidates, to represent the threshold value for the interface between the impression material and the other material.

7. A method as claimed in claim 1, wherein using said threshold value in generating a surface of said impression of an intra-oral anatomy includes:
   using the threshold value to classify the CT scanning results of the impression of an intra-oral anatomy either to represent the impression material or the other material; and
   generating the surface of the impression of an intra-oral anatomy using said classified CT scanning results which represent either the impression material or the other material by means of an appropriate algorithm, such as a marching cubes algorithm.

8. A method as claimed in claim 1, wherein the impression of an intra-oral anatomy is an impression of the surface of at least a part of a dental arch.

9. A method as claimed in claim 1, wherein the other material is air.

10. A CT imaging apparatus comprising means for implementing a method as claimed in claim 1.

11. An apparatus as claimed in claim 10, wherein the CT imaging apparatus is a dental CBCT apparatus.

12. A calibration tool for providing a recess or a hole to an impression material, the calibration tool comprising at least a part having a predetermined dimensions, the part being for providing a recess or a hole for use in a method as claimed in claim 1.

13. An impression tray comprising a first volume for impression material for teeth and a second volume for impression material for a calibration tool as claimed in claim 12.

14. An impression tray as claimed in claim 13, the impression tray further comprising the calibration tool.

15. An impression tray as claimed in claim 13, wherein said first volume is of a shape of an arch, and said second volume is arranged on one of an area inside that arch and on a handle formed on said tray.

* * * * *